(12) United States Patent
Zhang et al.

(10) Patent No.: US 12,006,310 B2
(45) Date of Patent: Jun. 11, 2024

(54) PREPARATION AND APPLICATION OF TRITERPENOIDS WITH EFFECT OF IMPROVING GLUCOSE AND LIPID METABOLISM DISORDERS

(71) Applicant: SERICULTURAL & AGRI-FOOD RESEARCH INSTITUTE GUANGDONG ACADEMY OF AGRICULTURAL SCIENCES, Guangzhou (CN)

(72) Inventors: Mingwei Zhang, Guangzhou (CN); Yuanyuan Deng, Guangzhou (CN); Guang Liu, Guangzhou (CN); Yan Zhang, Guangzhou (CN); Zhencheng Wei, Guangzhou (CN); Pengfei Zhou, Guangzhou (CN); Ping Li, Guangzhou (CN); Zhihao Zhao, Guangzhou (CN); Xuchao Jia, Guangzhou (CN); Xiaojun Tang, Guangzhou (CN)

(73) Assignee: SERICULTURAL & AGRI-FOOD RESEARCH INSTITUTE GUANGDONG ACADEMY OF AGRICULTERAL SCIENCES, Guangzhou (CN)

( * ) Notice: Subject to any disclaimer, the term of this patent is extended or adjusted under 35 U.S.C. 154(b) by 0 days.

(21) Appl. No.: 17/855,823

(22) Filed: Jul. 1, 2022

(65) Prior Publication Data
US 2023/0022783 A1    Jan. 26, 2023

(51) Int. Cl.
*C07D 407/12*    (2006.01)
*A61K 36/42*    (2006.01)

(52) U.S. Cl.
CPC ............ *C07D 407/12* (2013.01); *A61K 36/42* (2013.01)

(58) Field of Classification Search
CPC ............................ A61K 36/42; C07D 407/12
(Continued)

(56) References Cited

FOREIGN PATENT DOCUMENTS

CN    111067094 A    *    4/2020    ............. A23L 33/10

OTHER PUBLICATIONS

Machine Translation of CN111067094A, Google patents, retrieved Sep. 2023 (Year: 2023).*
(Continued)

*Primary Examiner* — Jeffrey S Lundgren
*Assistant Examiner* — Heather Raquel Dahlin
(74) *Attorney, Agent, or Firm* — Reising Ethington P.C.

(57) ABSTRACT

The present invention relates to the technical field of natural medicines, and in particular to a triterpenoid compound with an effect of improving glucose and lipid metabolism disorders, and preparation and application thereof. A novel triterpenoid compound was obtained by separation from *Momordica charantia* L. for the first time in the present invention. Studies on a mouse primary hepatocyte model and a 3T3-L1 preadipocyte model show that the novel triterpenoid compound in the present invention has activity of regulating glucose and lipid metabolism, and after combination with known triterpenoid compound Momordicoside G, the activity of regulating glucose and lipid metabolism is significantly higher than that of a single compound at the same dose, indicating that the novel triterpenoid compound and a complex thereof in the present invention can be used to improve glucose and lipid metabolism disorders and provide a new way for diabetes treatment.

2 Claims, 10 Drawing Sheets

(58) Field of Classification Search
USPC .......................................................... 514/451
See application file for complete search history.

(56) References Cited

OTHER PUBLICATIONS

Yue J, Xu J, Cao J, Zhang X, Zhao Y. Cucurbitane triterpenoids from *Momordica charantia* L. and their inhibitory activity against α-glucosidase, α-amylase and protein tyrosine phosphatase 1B (PTP1B). Journal of Functional Foods. Oct. 1, 2017;37:624-31. (Year: 2017).*

Shivanagoudra SR, Perera WH, Perez JL, Athrey G, Sun Y, Wu CS, Jayaprakasha GK, Patil BS. In vitro and in silico elucidation of antidiabetic and anti-inflammatory activities of bioactive compounds from *Momordica charantia* L. Bioorganic & Medicinal Chemistry . Jul. 15, 2019;27(14):3097-109. (Year: 2019).*

* cited by examiner

PREPARATION AND APPLICATION OF TRITERPENOIDS WITH EFFECT OF IMPROVING GLUCOSE AND LIPID METABOLISM DISORDERS

TECHNICAL FIELD

The present invention relates to the technical field of natural medicines, and in particular, to a triterpenoid compound with an effect of improving glucose and lipid metabolism disorders, and preparation and application thereof.

BACKGROUND

Diabetes is a common chronic non-communicable disease that has become a serious worldwide public health problem. Persistent hyperglycemia of diabetic patients probably leads to a series of microvascular or macrovascular complications, involving eyes, kidneys, the heart, the nervous system, and the like, and consequent decline in quality of life and high medical expenses will lead to serious economic burden and disease burden.

In recent years, diabetes has become a chronic disease which is second only to tumor diseases and cardiovascular diseases, and is relatively harmful to human health and safety. At present, α-glucosidase inhibitor acarbose tablets, insulin secretion-promoting agents, and the like are widely used clinically as pharmaceutical preparations for treatment of diabetes. These chemosynthetic drug inhibitors intervene and regulate mainly for a single pathway. However, recent studies at home and abroad show that overweight and obesity are closely related to diabetes, and the risk for diabetes in overweight people is 2-3 times that for people with a normal weight. In 2020, related content of weight management of people suffering from diabetes was added in the latest edition of Guideline for the Prevention and Treatment of Type 2 Diabetes Mellitus in China issued by Chinese Diabetes Society. Weight management is beneficial to blood glucose control and delays progression of diabetes. Scientific research has shown that improving lipid metabolic disorders is conducive to better control over blood glucose levels. Natural products with activity of regulating glucose metabolism and lipid metabolism have become an important source of diabetes prevention and treatment drugs.

*Momordica charantia* L. is a tropical-subtropical characteristic medicinal and edible vegetable, which is mainly used for treatment of diseases such as diabetes and cancer in traditional Chinese medicine. However, the composition and structure of main active substances of its health effect are not clear, and a mechanism of hypoglycemic effect is not clear. Therefore, it is of great significance to find active substances with health effects from *Momordica charantia* L.

SUMMARY

To overcome the shortcomings of the prior art, a novel triterpenoid compound was obtained by separation from plant *Momordica charantia* L. for the first time in the present invention. The compound has a function of improving glucose and lipid metabolism disorders and can be used for treating diabetes.

To achieve the foregoing objective, the technical solution used in the present invention is as follows:

The present invention provides a novel triterpenoid compound, and the triterpenoid compound has a structure shown in formula (I):

The novel triterpenoid compound was named (23R, 25E)-3β-hydroxy-23-methoxycucurbita-6,25-dien-5β,19-olide3-O-β-d-allopyranoside.

The present invention further provides a method for preparing the foregoing novel triterpenoid compound, including the following steps:

S1: cleaning fresh *Momordica charantia* L., removing seeds, slicing, drying, pulverizing and sieving to obtain dry *Momordica charantia* L. powder;

S2: extracting the dry *Momordica charantia* L. powder with ethanol to obtain *Momordica charantia* L. triterpenoid extract;

S3: extracting the *Momordica charantia* L. triterpenoid extract with petroleum ether, ethyl acetate, and n-butanol, and concentrating to obtain a petroleum ether phase, an ethyl acetate phase, and a n-butanol phase in sequence;

S4: after crude purification of the n-butanol phase with D101 macroporous resin, eluting with water, an ethanol-water solution with a volume percentage of 20%, and an ethanol-water solution with a volume percentage of 80% in sequence, where an elution part of the ethanol-water solution with a volume percentage of 80% is a triterpenoid enriched part;

S5: separating and purifying the elution part of the ethanol-water solution with a volume percentage of 80% by a normal phase silica gel column, using chloroform/methanol as an eluent, and eluting with chloroform/methanol with a volume ratio of 50:1 and chloroform/methanol with a volume ratio of 20:1 in sequence;

S6: collecting the chloroform/methanol eluent with a volume ratio of 20:1, separating by reversed-phase column chromatography, and then performing gradient eluting with methanol aqueous solutions with volume percentages of 50% and 60% respectively; and S7: collecting a gradient eluent of the methanol aqueous solution with a volume percentage of 60%, separating by dextran gel LH-20 chromatography, eluting with methanol to obtain a methanol eluent, further purifying the methanol eluent by a high performance liquid chromatograph, and eluting with methanol with a volume percentage of 95% to obtain the novel triterpenoid compound.

Preferably, the ethanol in step S2 is ethanol with a volume percentage of 70%.

Preferably, in step S3, a volume ratio of the *Momordica charantia* L. triterpenoid extract to the petroleum ether, a volume ratio of the *Momordica charantia* L. triterpenoid extract to the ethyl acetate, and a volume ratio of the *Momordica charantia* L. triterpenoid extract to the n-butanol are all 1:3.

The present invention further provides application of the foregoing novel triterpenoid compound in preparation of a drug for treatment of diabetes.

In the present invention, primary hepatocytes of mice were used as a model to analyze hepatic gluconeogenesis inhibitory activity of the foregoing novel triterpenoid compound. Research results showed that hepatic gluconeogenesis inhibitory activity of the novel triterpenoid compound at concentrations of 20 μM and 40 μM were 32.09% and 28.88%, respectively. Hepatic gluconeogenesis inhibitory activity of known triterpenoid compound Momordicoside G at concentrations of 20 μM and 40 μM were 20.75% and 34.42%, respectively. After combination of the two at 1:0.5, the hepatic gluconeogenesis inhibitory activity at concentrations of 20 μM and 40 μM were 36.58% and 38.36%, respectively; after combination of the two at 1:1, the hepatic gluconeogenesis inhibitory activity at concentrations of 20 μM and 40 μM were 34.47% and 40.61%, respectively; and after combination of the two at 1:1.5, the hepatic gluconeogenesis inhibitory activity at concentrations of 20 μM and 40 μM were 32.55% and 42.36%, respectively. This was superior to berberine (a main component of traditional Chinese herbal medicine Coptidis *rhizoma*) having an inhibition rate of 15.61% at 20 μM and an inhibition rate of 35.18% at 40 μM, and the hepatic gluconeogenesis inhibitory activity was remarkable.

In addition, 3T3-L1 preadipocytes were used as a model to analyze an impact of the foregoing novel triterpenoid compound on adipocyte differentiation. Research results showed that inhibition rates on differentiation of 3T3-L1 preadipocytes of the novel triterpenoid compound at concentrations of 20 μM and 40 μM were 35.48% and 56.42%, respectively. Inhibition rates on differentiation of 3T3-L1 preadipocytes of known triterpenoid compound Momordicoside G at concentrations of 20 μM and 40 μM were 23.77% and 51.27%, respectively. After combination of the two at 1:0.5, the inhibition rates on differentiation of 3T3-L1 preadipocytes at concentrations of 20 μM and 40 μM were 37.62% and 60.59%, respectively; after combination of the two at 1:1, the inhibition rates on differentiation of 3T3-L1 preadipocytes at concentrations of 20 μM and 40 μM were 40.41% and 65.20%, respectively; and after combination of the two at 1:1.5, the inhibition rates on differentiation of 3T3-L1 preadipocytes at concentrations of 20 μM and 40 μM were 36.66% and 58.82%, respectively. The adipocyte differentiation inhibitory activity was remarkable.

The foregoing research results show that the novel triterpenoid compound according to the present invention has the effect of improving glucose and lipid metabolism disorders. In addition, after combination with the triterpenoid compound Momordicoside G, the effect of improving glucose and lipid metabolism disorders was significantly higher than that of a single compound at the same dose. This indicates that the novel triterpenoid compound according to the present invention can be used for treatment of hyperglycemia and hyperlipidemia caused by diabetes.

The present invention further provides a drug for treatment of diabetes, where the drug includes the foregoing novel triterpenoid compound.

The present invention further provides a drug for treatment of diabetes, where the drug includes the forgoing novel triterpenoid compound and triterpenoid compound Momordicoside G.

Preferably, a mass ratio of the novel triterpenoid compound to the triterpenoid compound Momordicoside G is 1:(0.5-1.5).

Further, the mass ratio of the novel triterpenoid compound to the triterpenoid compound Momordicoside G is 1:0.5, 1:1.0, or 1:1.5.

Preferably, to improve the applicable scope of the drug, the foregoing two drugs further include a pharmaceutically acceptable carrier and/or excipient. The carrier and/or the excipient include/includes an acidulant, a toner, a flavor, a sweetener, or a combination thereof.

Preferably, dosage forms of the foregoing two drugs include, but are not limited to, an injection, an oral liquid, a tablet, an instant medicine to be mixed with water before administration, a granule, a capsule, and a pill.

In addition, the novel triterpenoid compound according to the present invention can be further used as a functional ingredient of a special health or health-care food for diabetics.

Compared with the prior art, the present invention has the following beneficial effects:

In the present invention, studies on a mouse primary hepatocyte model and a 3T3-L1 preadipocyte model show that the novel triterpenoid compound according to the present invention has an effect of significantly improving glucose and lipid metabolism disorders when used alone or in combination with the triterpenoid compound Momordicoside G, indicating that the novel triterpenoid compound and a complex thereof according to the present invention can achieve the objective of multi-way collaborative treatment of diabetes by regulating blood glucose and blood lipid metabolism, and provide a novel way for treatment of glucose and lipid metabolism diseases such as diabetes. In addition, the compound according to the present invention is derived from vegetable *Momordica charantia* L., and has high safety, small side effects and wide application prospects.

DESCRIPTION OF EMBODIMENTS

Specific implementations of the present invention are further described below. It should be noted here that the descriptions of these implementations are used to help understand the present invention, but do not constitute a limitation on the present invention. In addition, the technical features involved in various implementations of the present invention described below may be combined with each other provided that no conflict with each other occurs.

Experimental methods in the following embodiments are conventional unless otherwise specified, and experimental materials used in the following embodiments may be purchased through conventional commercial channels unless otherwise specified.

Embodiment 1 Preparation of a Novel Triterpenoid Compound 1.1. Plant Source and Identification A fruit sample of *Momordica charantia* L., a plant material for extraction, is a green strip-tuberculate elongated *Momordica charantia* L., which was purchased from Guangzhou, Guangdong Province.

1.2. Extraction and Separation (1) Fresh *Momordica charantia* L. were cleaned, seeds were removed, and the *Momordica charantia* L. was sliced, dried, pulverized and sieved with a 40-mesh sieve to obtain dry *Momordica charantia* L. powder.

(2) The dry *Momordica charantia* L. powder was extracted at normal temperature with ethanol with a volume percentage of 70% at a solid-liquid ratio of 1:3 (g:mL) to obtain *Momordica charantia* L. triterpenoid extract.

(3) The *Momordica charantia* L. triterpenoid extract was mixed with petroleum ether, ethyl acetate, and n-butanol in sequence at a volume ratio of 1:3 and then shaken for 10 min, stood in a separating funnel at room temperature for 30 minutes until layering was implemented, and a triterpenoid enriched layer was separated and then concentrated to obtain a petroleum ether phase, an ethyl acetate phase, and a n-butanol phase in sequence.

(4) After crude purification of the n-butanol phase with D101 macroporous resin, eluting was performed with water, an ethanol-water solution with a volume percentage of 20%, and an ethanol-water solution with a volume percentage of 80% in sequence, where an elution part of the ethanol-water solution with a volume percentage of 80% was a triterpenoid enriched part.

(5) The elution part of the ethanol-water solution was separated and purified with a volume percentage of 80% by a normal phase silica gel column, chloroform/methanol was used as an eluent, and eluting was performed with chloroform/methanol with a volume ratio of 50:1 and chloroform/methanol with a volume ratio of 20:1 in sequence.

(6) The chloroform/methanol eluent with a volume ratio of 20:1 was collected and separated by reversed-phase column chromatography, and then gradient eluting was performed with methanol aqueous solutions with volume percentages of 50% and 60% respectively.

(7) A gradient eluent of the methanol aqueous solution with a volume percentage of 60% was collected, separated by dextran gel LH-20 chromatography, and eluted with methanol to obtain a methanol eluent. The methanol eluent was further purified by a high performance liquid chromatograph, and eluting was performed with methanol with a volume percentage of 95% to obtain the novel triterpenoid compound.

(8) The methanol eluent obtained through separation by dextran gel LH-20 chromatography in step (7) was further purified by the high performance liquid chromatograph, and eluting was performed with methanol with a volume percentage of 85% to obtain known triterpenoid compound Momordicoside G, with a structure shown in formula (II).

The triterpenoid compound obtained in step (7) was structurally identified in the Phytochemical Analysis and Testing Center of Kunming Institute of Botany, Chinese Academy of Sciences. The triterpenoid compound was white amorphous powder, $[\alpha]20\ D+39.0$ (c 0.1, $CH_3OH$); HR-ESI-MS (neg.), m/z 645.4012 $[M-H]^-$ (calcd for $C_{37}H_{57}O_9^-$, 645.4008), $^1H$ (500 MHz) and $^{13}C$ (125 MHz). Nuclear magnetic data of the triterpenoid compound is shown in Table 1.

TABLE 1 shows $^1H$ NMR and $^{13}C$ NMR data (in pyridine-d5) of the novel triterpenoid compound.

SPECIFICATION

| C/H | $\delta_H$ (mult., J in Hz) | $\delta_C$ (DEPT) |
|---|---|---|
| 1 | 1.46 (m) | 20.2 ($CH_2$) |
|   | 1.70 (m) | |
| 2 | 1.78 (m) | 26.9 ($CH_2$) |
|   | 2.44 (m) | |
| 3 | 3.62 (m) | 85.7 (CH) |
| 4 | | 38.8 (C) |
| 5 | | 84.7 (C) |
| 6 | 6.33 (d, 6.8) | 133.4 (CH) |
| 7 | 5.62 (dd, 6.8, 2.0) | 133.0 (CH) |
| 8 | 2.57 (m) | 45.3 (CH) |
| 9 | | 51.2 (C) |
| 10 | 2.68 (m) | 41.2 (CH) |
| 11 | 1.73 (m) | 22.4 ($CH_2$) |
|   | 2.43 (m) | |
| 12 | 1.62 (m) | 30.6 ($CH_2$) |
|   | 1.65 (m) | |
| 13 | | 45.8 (C) |
| 14 | | 48.4 (C) |
| 15 | 1.25 (m) | 33.8 ($CH_2$) |
| 16 | 1.40 (m) | 28.4 ($CH_2$) |
|   | 1.94 (m) | |
| 17 | 1.46 (m) | 51.8 (CH) |
| 18 | 0.91 (s) | 15.0 ($CH_3$) |
| 19 | | 182.5 (C) |
| 20 | 1.94 (m) | 33.3 (CH) |
| 21 | 1.05 (d, 5.4) | 19.3 ($CH_3$) |
| 22 | 1.03 (m) | 43.8 ($CH_2$) |
|   | 1.85 (m) | |
| 23 | 4.13 (m) | 75.2 (CH) |
| 24 | 5.24 (d, 6.2) | 128.4 (CH) |
| 25 | | 135.0 (C) |
| 26 | 1.76 (s) | 26.3 ($CH_3$) |
| 27 | 1.72 (s) | 18.6 ($CH_3$) |
| 28 | 0.91 (s) | 21.3 ($CH_3$) |
| 29 | 1.55 (s) | 24.2 ($CH_3$) |
| 30 | 0.84 (s) | 19.8 ($CH_3$) |
| 23-OMe | 3.30 (s) | 56.1 |

TABLE 1-continued shows $^1$H NMR and $^{13}$C NMR data (in pyridine-d5) of the novel triterpenoid compound.
SPECIFICATION

| C/H | $\delta_H$ (mult., J in Hz) | $\delta_C$ (DEPT) |
|---|---|---|
| 25-OMe | | |
| 1' | 5.32 (d, 5.6) | 105.5 (CH) |
| 2' | 3.90 (m) | 72.8 (CH) |
| 3' | 4.65 (m) | 73.6 (CH) |
| 4' | 4.14 (m) | 69.6 (CH) |
| 5' | 4.47 (m) | 76.4 (CH) |
| 6' | 4.42 (dd, 12.0, 5.3) | 63.8 (CH$_2$) |
|  | 4.53 (dd, 12.0, 2.7) | |

Based on comprehensive analysis of the foregoing spectrum-related data, a structural formula of the triterpenoid compound is parsed and deduced as shown in the following formula (I), which is named (23R, 25E)-3β-hydroxy-23-methoxycucurbita-6,25-dien-5β,19-olide3-O-β-D-allopyranoside.

Formula (I)

Formula (II)

Embodiment 2 Analysis of Effects of a Novel Triterpenoid Compound (23R, 25E)-3β-hydroxy-2β-methoxycucurbita-6, 25-dien-5β,19-olide3-O-β-D-allopyranoside and Momordicoside G on Improving Glucose and Lipid Metabolism Disorders 1. Hepatic Gluconeogenesis Inhibitory Activity In this embodiment, primary isolated hepatic parenchymal cells of SD rats (purchased from Experimental Animal Center of Southern Medical University) were used as a model, and berberine, a traditional Chinese medicine as a hypoglycemic agent, was used as a positive control to evaluate an impact of the novel triterpenoid compound (23R, 25E)-3β-hydroxy-23-methoxycucurbita-6,25-dien-5β,19-olide3-O-β-d-allopyranoside and Momordicoside G, and compositions thereof in different proportions (novel triterpenoid compound:Momordicoside G=1:0.5, 1:1.0, or 1:1.5) on hepatic gluconeogenesis, thereby further elaborating beneficial effects of the present invention. The process was as follows:

1.1. Experimental Cells

In-situ perfusion digestion was used to digest SD rat liver with type IV collagenase. After being dispersed, hepatocytes were transferred to a 49% Percoll separation solution for centrifugation. After supernatant was discarded, the cells adhered for 6 hours to a 24-well plate coated with 0.2% gelatin. After starvation in a serum-free low-sugar medium for 8 hours, the supernatant was discarded, the cells were washed with PBS buffer, and then a reaction solution (sugar-free DMEM containing 2 mM sodium pyruvate and 20 mM sodium lactate) was added, waiting for a sample test.

1.2. Test Method

Triterpenoid compounds (a novel triterpenoid compound and Momordicoside G) were dissolved in dimethyl sulfoxide (DMSO) to prepare 10 μM mother liquor. Through dilution with the foregoing reaction solution, the final concentrations of the triterpenoid compounds finally added into cell culture wells were 20 μM and 40 μM respectively, and the final concentration of the DMSO was 0.4%. A negative control was a reaction solution containing the DMSO with the same concentration (0.4%). Berberine, a positive control, was prepared into 40 mM with ultrapure water, the final concentrations for the test were 20 μM and 40 μM, and the final concentration of the DMSO was kept at 0.4%. To-be-tested samples were added into the cell reaction solution, and continued to be cultured for 6 hours. Then the glucose concentration in the culture medium (that is, the reaction solution) of each well was measured, and then the medium was discarded. After being washed with PBS, the cells were lysed with 250 mM NaOH, and the protein concentration was measured by using a Coomassie brilliant blue method. By reading an absorbance value, the concentration of glucose in the medium in all sample wells and the concentration of protein after lysis were determined by using a standard curve method, and a ratio of the two was used to measure an average gluconeogenesis level of the cells in the wells.

1.3. Experimental Results

For *Momordica charantia* L., hepatic gluconeogenesis inhibitory activity of the novel triterpenoid compound (23R, 25E)-3β-hydroxy-23-methoxycucurbita-6,25-dien-5β,19-olide3-O-β-d-allopyranoside at concentrations of 20 μM and 40 μM were 32.09% and 28.88%, respectively. Hepatic gluconeogenesis inhibitory activity of known compound Momordicoside G at concentrations of 20 μM and 40 μM were 20.75% and 34.42%, respectively. After combination of the novel compound and the known compound at 1:0.5, the hepatic gluconeogenesis inhibitory activity at concentrations of 20 μM and 40 μM were 36.58% and 38.36%, respectively; after combination at 1:1, the hepatic gluconeogenesis inhibitory activity at concentrations of 20 μM and 40 μM were 34.47% and 40.61%, respectively; and after combination at 1:1.5, the hepatic gluconeogenesis inhibitory activity at concentrations of 20 μM and 40 μM were 32.55% and 42.36%, respectively. This was superior to berberine (a main component of traditional Chinese herbal medicine Coptidis *rhizoma*) having an inhibition rate of 15.61% at 20 μM and an inhibition rate of 35.18% at 40 μM, and the hepatic gluconeogenesis inhibitory activity was more remarkable.

2. Inhibitory Activity Against 3T3-L1 Preadipocyte-Induced Differentiation 2.1. Experimental Cells A mouse embryonic fibroblast 3T3-L1 cell line (preadipocytes) was purchased from Shanghai Cell Bank, Chinese Academy of Sciences.

2.2. Test Method

In the test, samples fell into an undifferentiation control group (cultured with a normal DMEM), a negative control group (cultured with a DMEM containing a differentiation solution), and a sample intervention group [cultured with a DMEM containing a differentiation solution+a or 40 μM triterpenoid compound or triterpenoid composition (novel triterpenoid compound:Momordicoside G=0.5, 1.0, or 1.5)]. Differentiation was induced by using a methylisobutylxanthine, dexamethasone and insulin, (MDI) induction medium (the induction medium is a differentiation solution, and the differentiation solution includes a high-sugar DMEM containing 0.5 mmol/L IBMX, 1 μmol/L DEX, 10 mg/L insulin, and 10% FCS). 3T3-L1 preadipocytes were cultured in an incubator with 5% CO2 and 37° C. saturated humidity, and cultured in the DMEM containing 10% FCS until the density of monolayer adherent cells was greater than or equal to 90%. After being washed with Hanks' balanced salt solution (HBSS), the cells were digested by trypsin, and then inoculated into a 6-well culture plate (1×10$^5$ cells/well). After cell contact inhibition, a fresh DMEM containing 10% FCS was used for fusion culture for 2 days. On the 3$^{rd}$ day (that is, the 0$^{th}$ day of differentiation), the cells were cultured in the differentiation solution for culture, and 0.1% DMSO and a novel triterpenoid compound (23R, 25E)-3β-hydroxy-23-methoxycucurbita-6,25-dien-5β,19-olide3-O-β-d-allopyranoside with concentration gradients of 20 μM and 40 μM or known compound Momordicoside G or a composition of the two were added in the sample intervention group. 0.1% DMSO was added in the negative control group. On the 2$^{nd}$ day of differentiation, the medium was replaced with a DMEM containing only 10 mg/L insulin and 10% FCS, the samples of each group continued to be cultured, and the medium was replaced once every 2 days until the experiment ended on the 8$^{th}$ day of differentiation. After the experiment ended, the medium was discarded, the cells were washed twice with cold PBS, and the cells were fixed with 4% paraformaldehyde solution for 60 min. After paraformaldehyde was removed and PBS was added for washing, the fixed cells were stained with an oil red O dye kit (Solarbio, G1262-4) for 1 hour, and the cells were washed with 60% isopropanol for 3 times to remove the uncolored oil red O dye and were photographed for observation. After the observation, the cells were lysed with lysate (containing 4% NP-40), and an absorbance value at 490 nm was measured, and calculated by using an OD value.

2.3. Experimental Results

Figure 1:
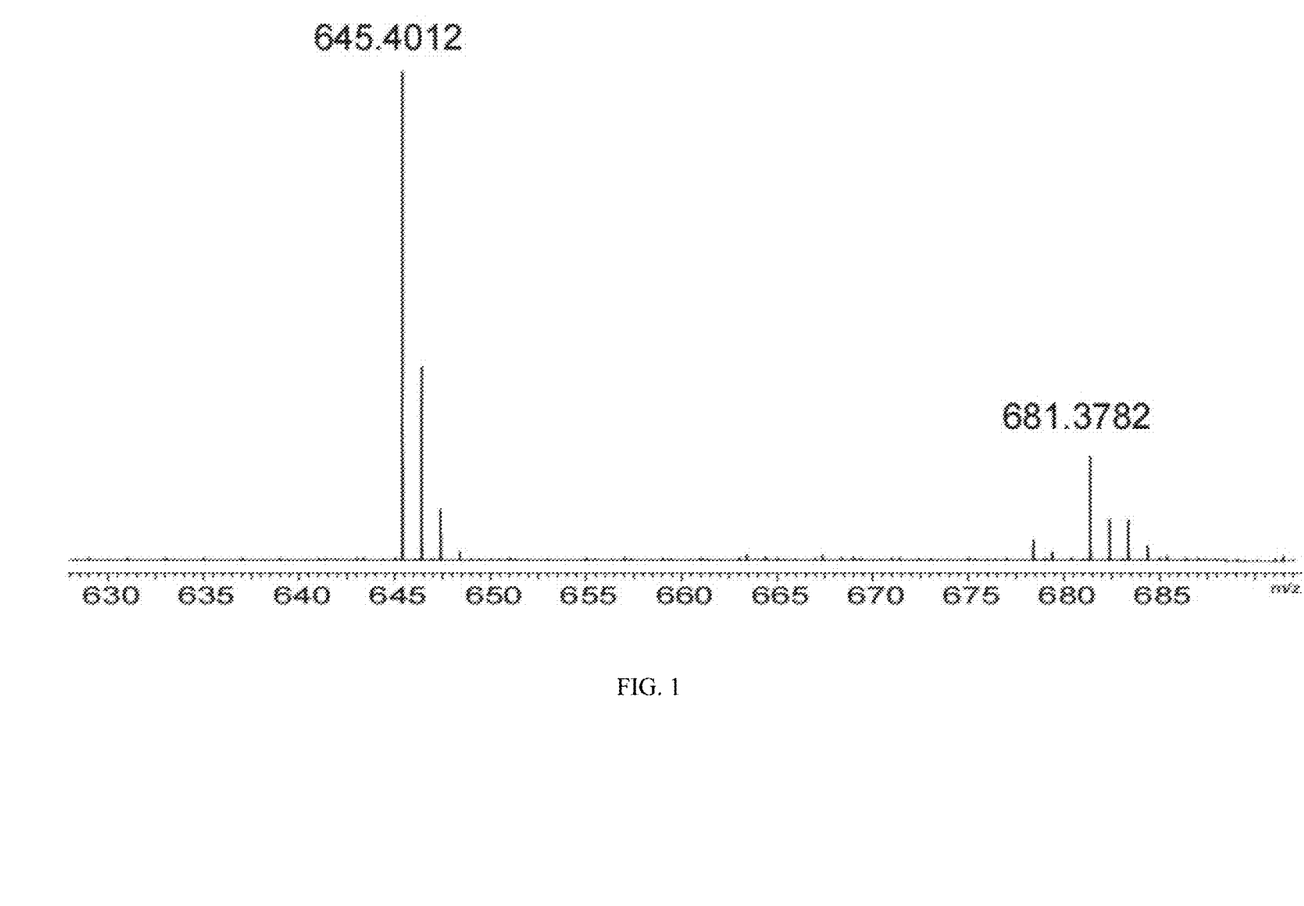
FIG. 1 is an HR-EI-MS spectrum (for determining a molecular weight of a novel compound) of a novel triterpenoid compound.
Figure 2:
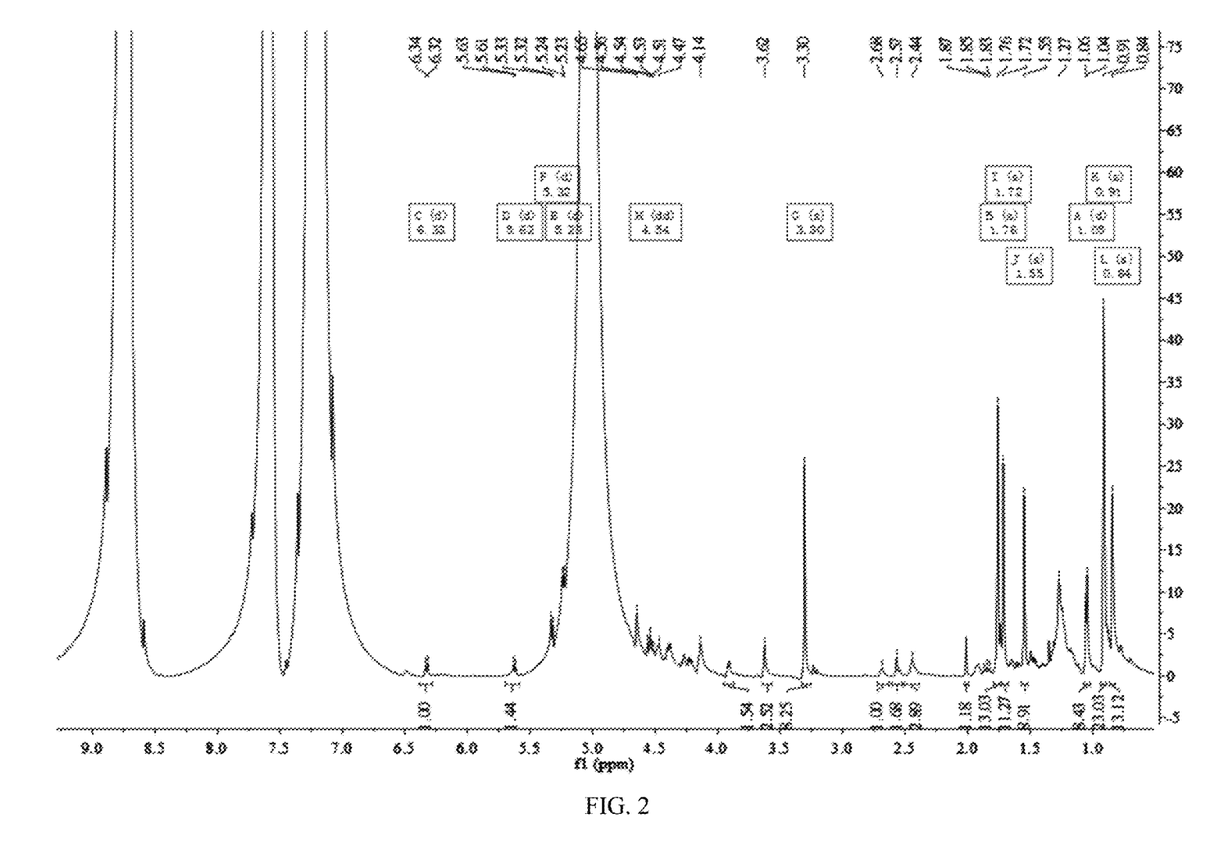
FIG. 2 is a $^1$H NMR spectrum (for determining proton types and quantities of a novel compound) of a novel triterpenoid compound.
Figure 3:
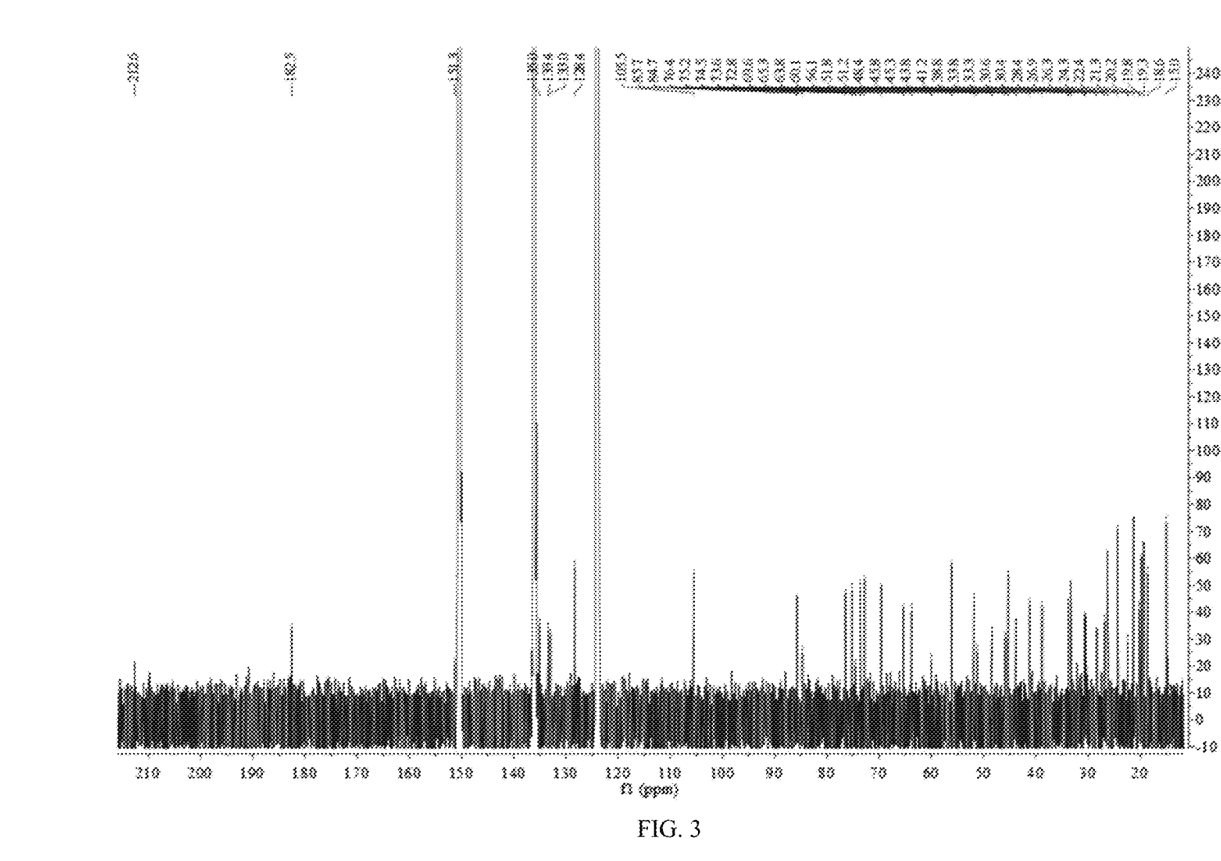
FIG. 3 is a $^{13}$C NMR spectrum (for determining carbon atom types and quantities of a novel compound) of a novel triterpenoid compound.
Figure 4:
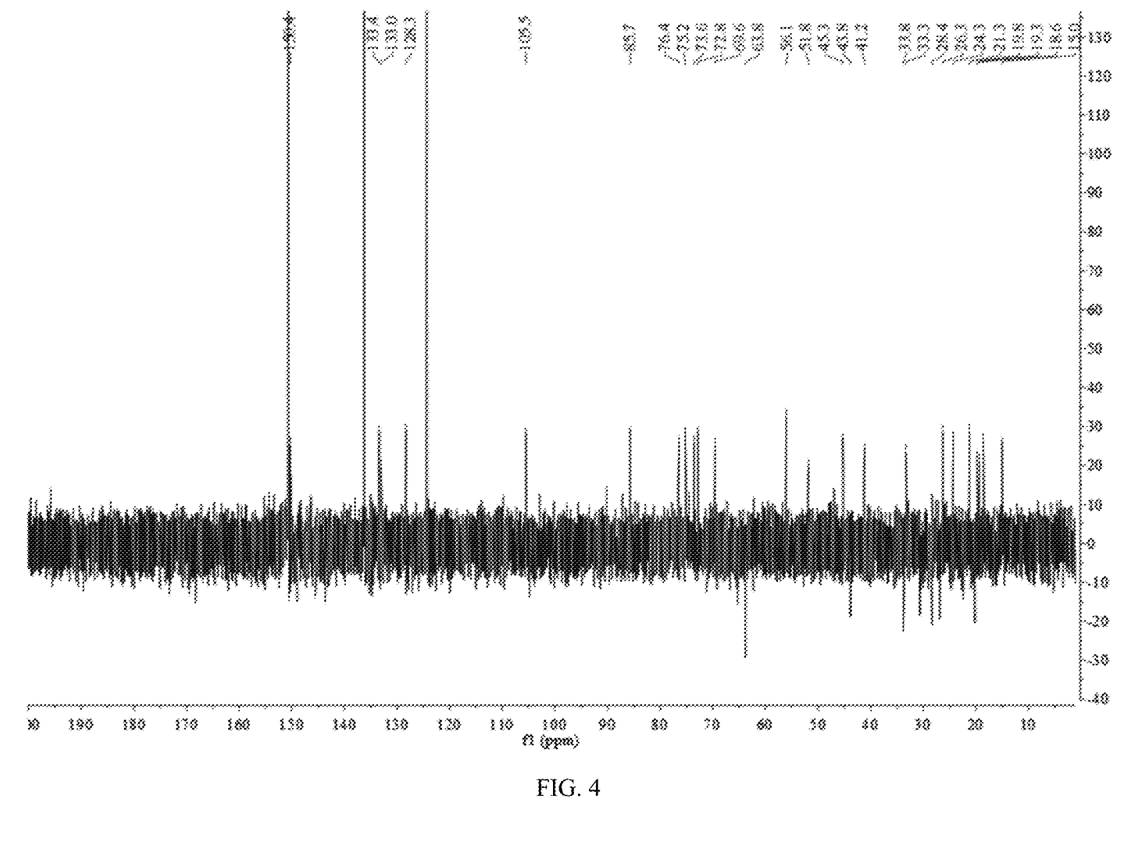
FIG. 4 is a DEPT135 spectrum (for determining secondary carbon and quaternary carbon in a structure of a novel compound) of a novel triterpenoid compound.
Figure 5:
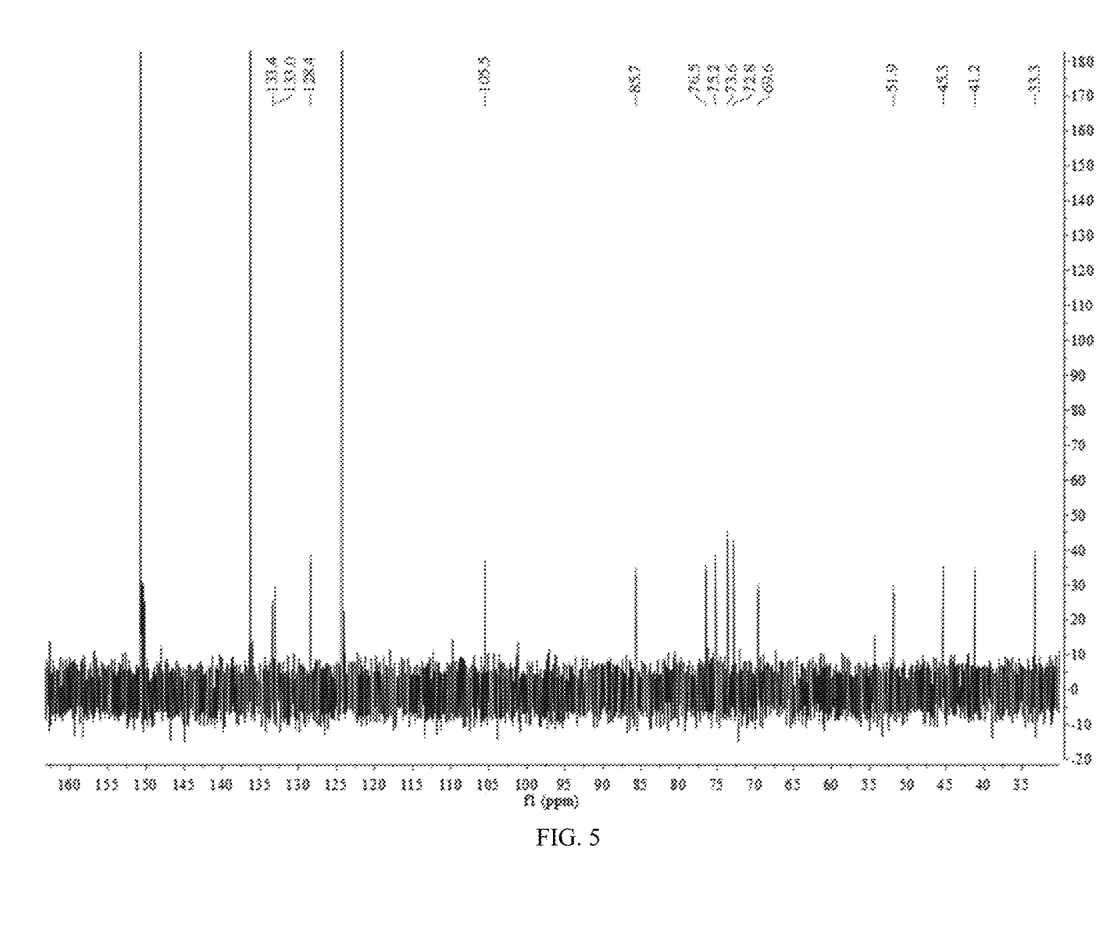
FIG. 5 is a DEPT90 spectrum (for determining a primary carbon and tertiary carbon of a structure of a novel compound with reference to DEPT135) of a novel triterpenoid compound.
Figure 6:
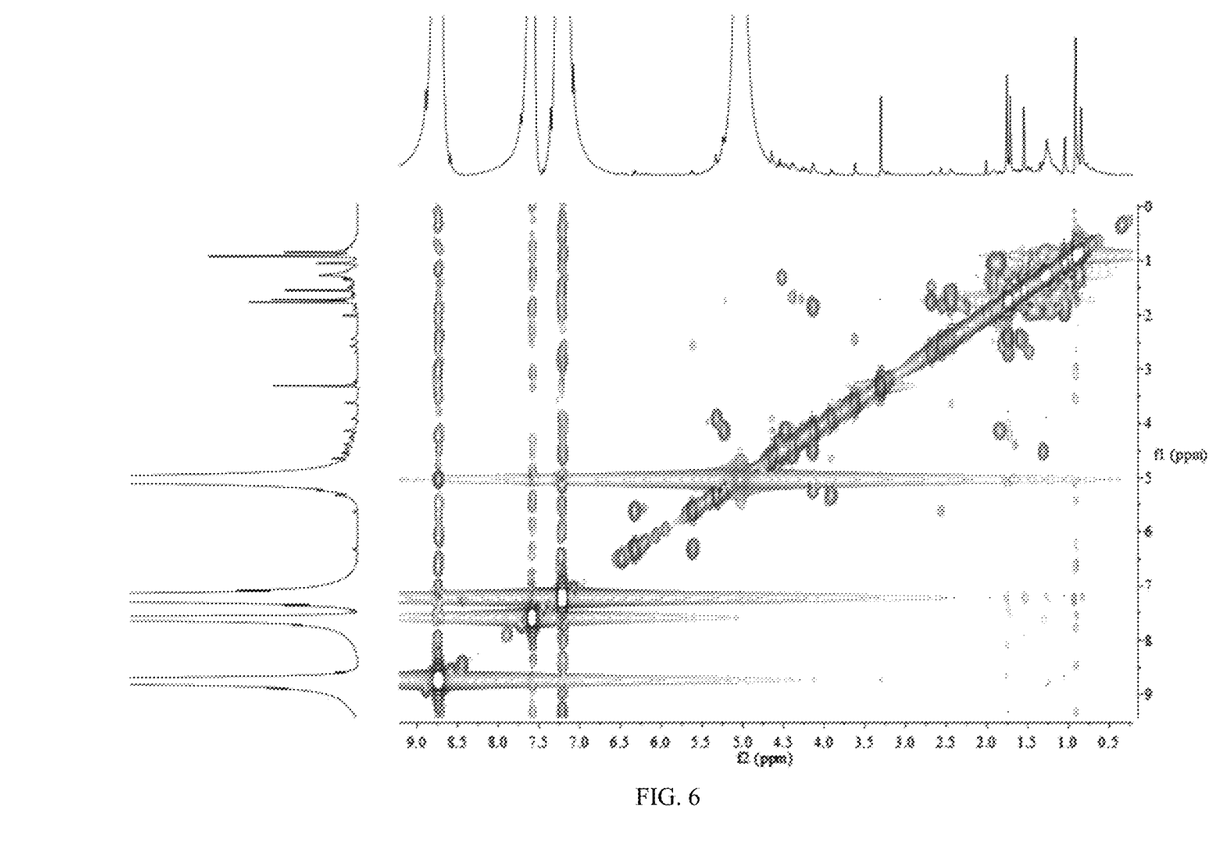
FIG. 6 is a $^1$H-$^1$H COSY spectrum (for determining a mutual coupling relationship between adjacent protons in a structure of a novel compound) of a novel triterpenoid compound.
Figure 7:
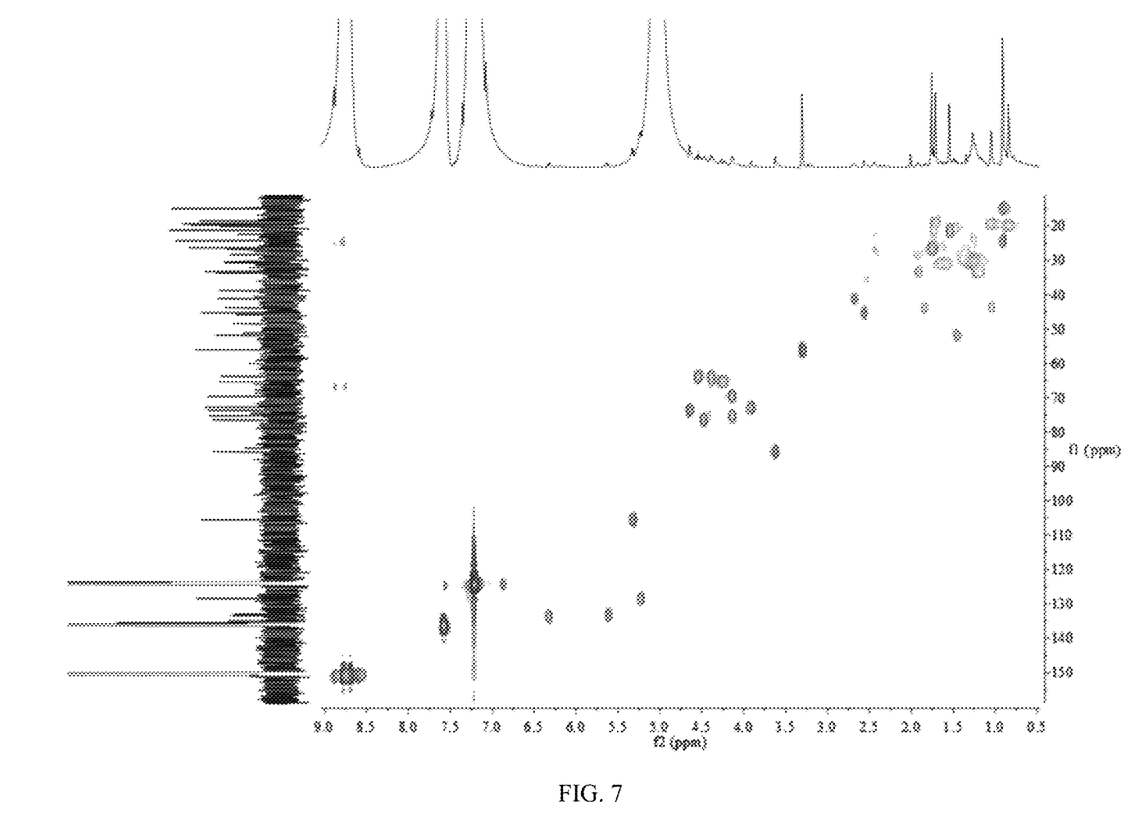
FIG. 7 is an HSQC spectrum (for determining a directly connected hydrocarbon relationship in a structure of a novel compound) of a novel triterpenoid compound.
Figure 8:
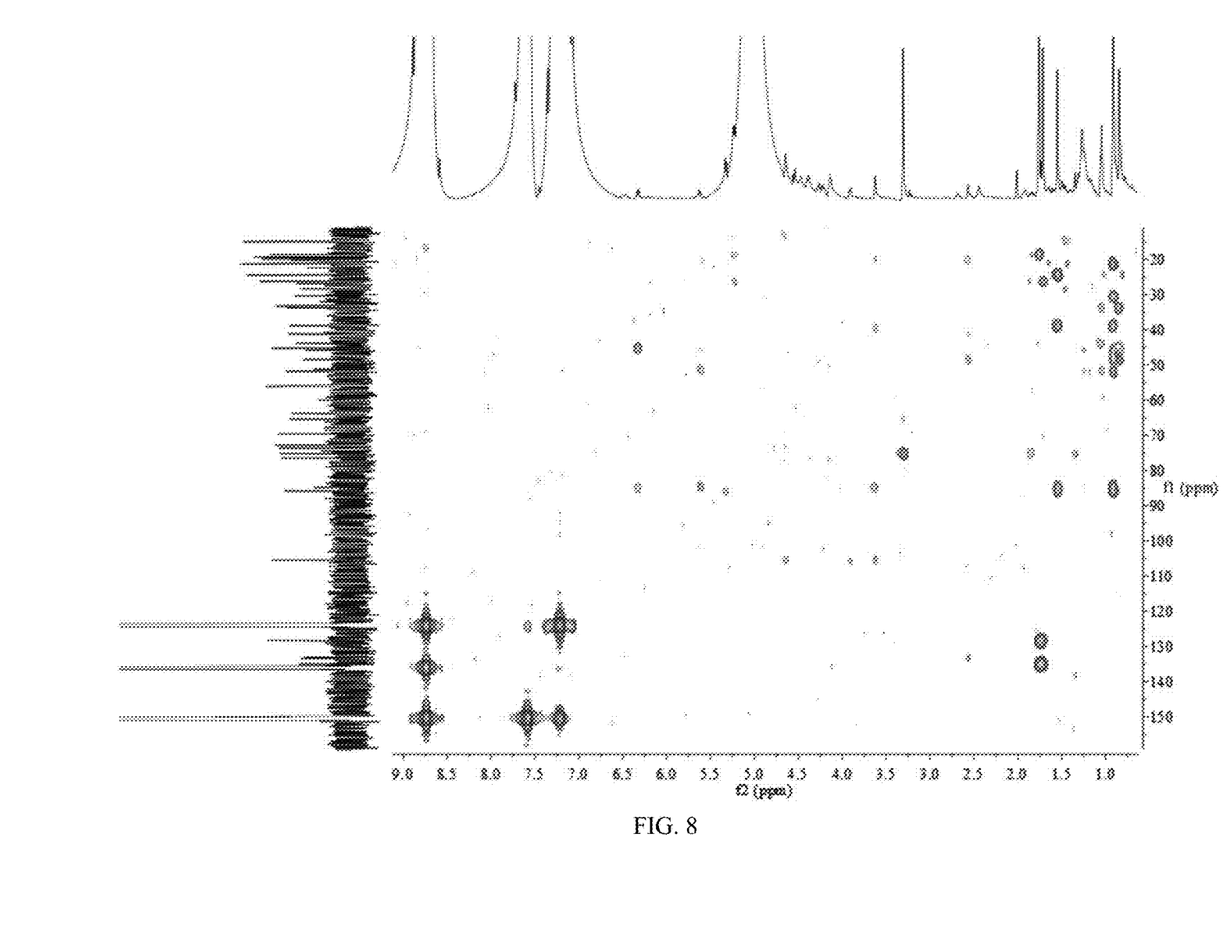
FIG. 8 is an HMBC spectrum (for determining a remote hydrocarbon coupling relationship in a structure of a novel compound) of a novel triterpenoid compound.
Figure 9:
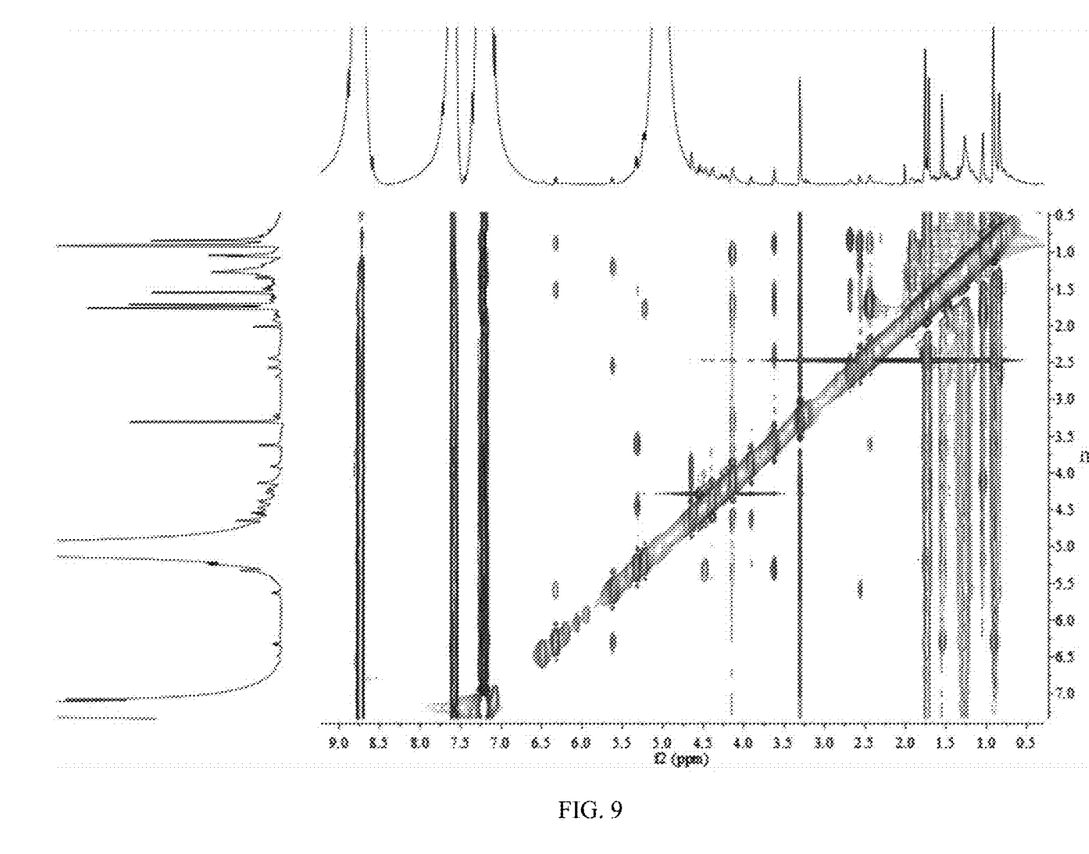
FIG. 9 is a TOCSY spectrum (for determining a spatial coupling relationship between protons in a structure of a novel compound) of a novel triterpenoid compound.
Figure 10:
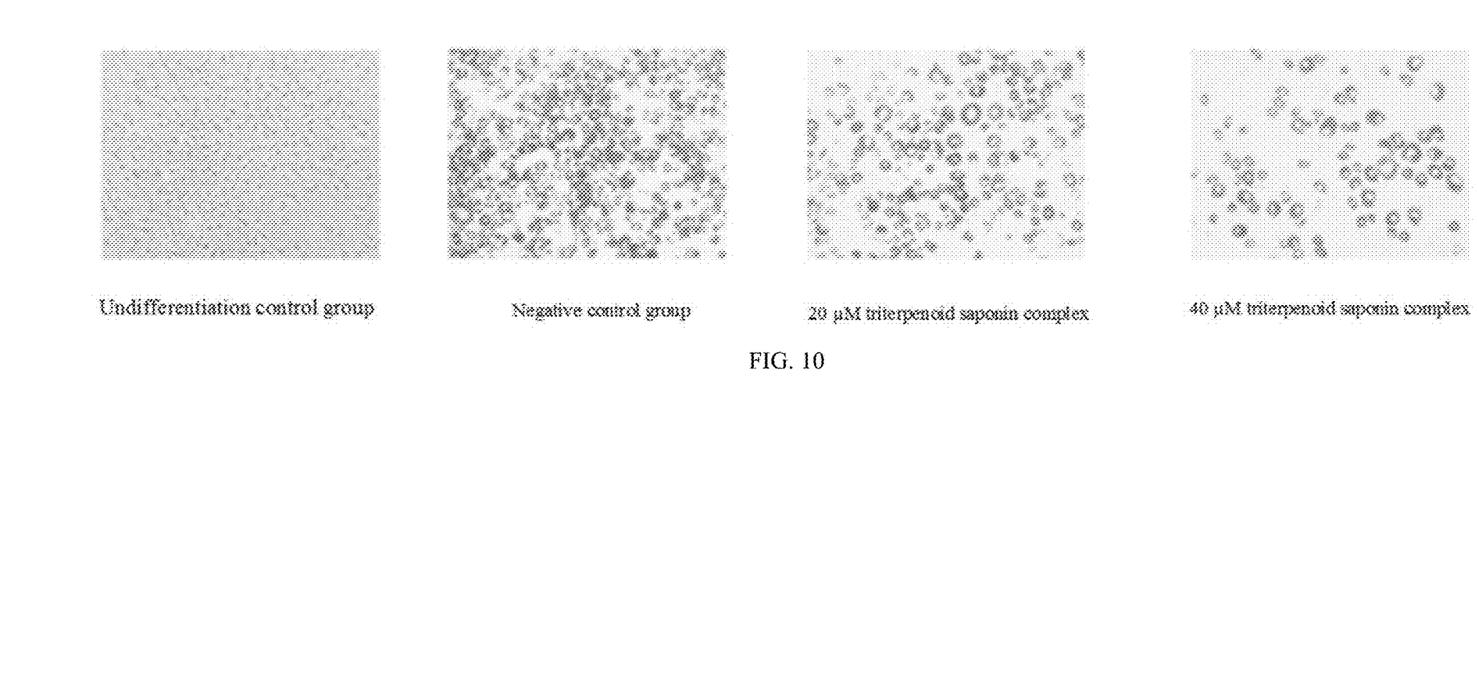
FIG. 10 shows results of oil red O staining after 3T3-L1 induced differentiation for 8 days (triterpenoid complex: novel triterpenoid compound and known triterpenoid compound Momordicoside G are compounded at 1:1).

After oil red O staining, compared with an undifferentiation solution group (control group), adipocytes in a differentiation solution group became larger and the content of intracellular lipid droplets increased significantly. In groups in which novel triterpenoid compound (23R, 25E)-3β-hydroxy-23-methoxycucurbita-6,25-dien-5β,19-olide3-O-β-d-allopyranoside at different concentrations (20 μM and 40 μM) or the known triterpenoid compound Momordicoside G or a composition of the two were added, compared with those of the differentiation solution group, the content of lipid droplets decreased significantly, and the differentiation of adipocytes decreased in a dose-dependent manner. Compared with that of the differentiation solution group, the inhibition rates of the novel triterpenoid compound (23R, 25E)-3β-hydroxy-23-methoxycucurbita-6, 25-dien-5β,19-olide3-O-β-d-allopyranoside on differentiation of 3T3-L1 preadipocytes at concentrations of 20 μM and 40 μM were 35.48% and 56.42%, respectively; the inhibition rates of the known triterpenoid compound Momordicoside G on differentiation of 3T3-L1 preadipocytes at concentrations of 20 μM and 40 μM were 23.77% and 51.27%, respectively; after the novel compound and the known compound were combined at 1:0.5, the inhibition rates on differentiation of 3T3-L1 preadipocytes at concentrations of 20 μM and 40 μM were 37.62% and 60.59%, respectively; after the novel compound and the known compound were combined at 1:1, the inhibition rates on differentiation of 3T3-L1 preadipocytes at concentrations of 20 μM and 40 μM were 40.41% and 65.20%, respectively; after the novel compound and the known compound were combined at 1:1.5, the inhibition rates on differentiation of 3T3-L1 preadipocytes at concentrations of 20 μM and 40 μM were 36.66% and 58.82%, respectively; and the adipocyte differentiation inhibitory activity was remarkable. This indicates that the novel triterpenoid compound (23R,25E)-3β-hydroxy-23-methoxycucurbita-6,25-dien-5β,19-olide3-O-β-d-allopyranoside and the known triterpenoid compound Momordicoside G can inhibit differentiation of 3T3-L1 preadipocytes and accumulation of intracellular lipids, and the effect is better when the two are compounded at a ratio. This shows that the triterpenoid complex can effectively inhibit adipocyte differentiation.

The implementations of the present invention have been described above in detail, but the present invention is not limited to the described implementations. For a person skilled in the art, various changes, modifications, replacements, and alterations made to these implementations without departing from the principle and spirit of the present invention still fall within the protection scope of the present invention.

What is claimed is:

1. A drug for treatment of diabetes, comprising a triterpenoid having a structure shown in formula (I) and a triterpenoid compound Momordicoside G, Formula (I)

wherein the mass ratio of the triterpenoid compound of formula (I) to the triterpenoid compound Momordicoside G is 1:(0.5-1.5).

2. The drug for treatment of diabetes according to claim 1, wherein the mass ratio of the triterpenoid compound of formula (I) to the triterpenoid compound Momordicoside G is 1:0.5, 1:1.0, or 1:1.5.

* * * * *